United States Patent
Toyos

(10) Patent No.: US 10,272,256 B2
(45) Date of Patent: Apr. 30, 2019

(54) SELECTED LIGHT WAVELENGTHS AND DELIVERY DEVICES FOR THE PREVENTION AND TREATMENT OF DRY EYE SYNDROME

(71) Applicant: Rolando Toyos, Germantown, TN (US)

(72) Inventor: Rolando Toyos, Germantown, TN (US)

( * ) Notice: Subject to any disclaimer, the term of this patent is extended or adjusted under 35 U.S.C. 154(b) by 349 days.

(21) Appl. No.: 14/411,631

(22) PCT Filed: Jul. 24, 2013

(86) PCT No.: PCT/US2013/051836
§ 371 (c)(1),
(2) Date: Dec. 29, 2014

(87) PCT Pub. No.: WO2014/018640
PCT Pub. Date: Jan. 30, 2014

(65) Prior Publication Data
US 2015/0174425 A1 Jun. 25, 2015

Related U.S. Application Data

(60) Provisional application No. 61/792,863, filed on Mar. 15, 2013, provisional application No. 61/675,790, filed on Jul. 25, 2012.

(51) Int. Cl.
*A61N 5/06* (2006.01)
*C12N 13/00* (2006.01)
*A61B 17/22* (2006.01)

(52) U.S. Cl.
CPC ...... *A61N 5/0616* (2013.01); *A61B 17/22012* (2013.01); *A61N 5/0613* (2013.01);
(Continued)

(58) Field of Classification Search
USPC .................... 606/2–19; 607/88–92
See application file for complete search history.

(56) References Cited

U.S. PATENT DOCUMENTS

2005/0197681 A1* 9/2005 Barolet ............... A61B 18/203
607/86
2006/0235370 A1 10/2006 Oblong et al.
(Continued)

FOREIGN PATENT DOCUMENTS

RU 2377965 C1 1/2010

OTHER PUBLICATIONS

Ion Laser, Wikipedia, https://en.wikipedia.org/wiki/Ion_laser, access Jul. 10, 2017.*
(Continued)

*Primary Examiner* — Carl H Layno
*Assistant Examiner* — Dacheng Xie
(74) *Attorney, Agent, or Firm* — Dinsmore & Shohl LLP

(57) ABSTRACT

Provided are methods and systems for treating or preventing dry eye syndrome in a subject. The methods involve applying light of a set of photomodulating parameters to the region of the eyelid. The light of these particular photomodulating parameters will increase the production of collagen, elastin or both thereby improving the tone of the eyelid. Improved eyelid tone will increase the level of meibum secreted through the meibomian duct thereby treating or preventing dry eye syndrome. Particular apparatuses are provided that emit and locate light of the necessary photomodulating parameters tailored for delivery to the eyelid areas activating fibroblasts specifically in this area and thereby improving eyelid tone and meibomian gland function.

20 Claims, 6 Drawing Sheets

(52) U.S. Cl.
CPC ...... *C12N 13/00* (2013.01); *A61N 2005/0643* (2013.01); *A61N 2005/0648* (2013.01); *A61N 2005/0652* (2013.01); *A61N 2005/0663* (2013.01)

(56) References Cited

U.S. PATENT DOCUMENTS

| | | | |
|---|---|---|---|
| 2007/0091265 A1* | 4/2007 | Kardon | A61B 3/0058 351/206 |
| 2011/0130729 A1* | 6/2011 | Korb | A61F 9/00772 604/294 |
| 2012/0016275 A1* | 1/2012 | Korb | A61F 9/00772 601/17 |
| 2012/0065556 A1* | 3/2012 | Smith | A61F 7/007 601/89 |
| 2013/0110101 A1* | 5/2013 | Van Valen | A61F 9/00718 606/33 |

OTHER PUBLICATIONS

Ti-sapphire Laser, Wikipedia, https://en.wikipedia.org/wiki/Ti-sapphire_laser, access Jul. 10, 2017.*

Goto, E., et al., "Treatment of non-inflamed obstructive meibomian gland dysfunction by an infrared warm compression device," Br J Ophthalmol 86: pp. 1403-1407 (2002).

International Search Report and Written Opinion for co-pending PCT application No. PCT/US2013/051836, filed Jul. 24, 2013.

* cited by examiner

SELECTED LIGHT WAVELENGTHS AND DELIVERY DEVICES FOR THE PREVENTION AND TREATMENT OF DRY EYE SYNDROME

CROSS REFERENCE TO RELATED APPLICATIONS

This application is the U.S. national phase of PCT/US2013/051836 filed Jan. 24, 2013, which depends from and claims priority to U.S. Provisional Application No. 61/675,490 filed Jul. 25, 2012, and U.S. Provisional Application No. 61/792,863 filed Mar. 15, 2013, all of which are incorporated herein by reference.

FIELD OF THE INVENTION

The invention relates to normal or pathological gland function. More specifically, the invention is related to methods to maintain normal meibomian gland function or prevent obstruction or occlusion of the meibomian gland. The invention also related to devices capable of targeting electromagnetic energy to a subject useful for the treatment or prevention of dry eye syndrome.

BACKGROUND OF THE INVENTION

Maintaining a proper balance of tear film components is essential for the health of the eye. Normal tear film requires proper amounts of lipid, aqueous and mucin components. The meibomian glands located in both the upper and lower eyelids include various sac-like acini are responsible for secretion of lipid components of tear film known as meibum or sebum into the duct of the gland. The meibum then passes into the orifices surrounded by smooth muscle tissue and the muscle of Riolan, which are presumed to aid in the expression of meibum onto the eye surface. It is believed that the meibomian gland orifices open during a normal blinking reflex to release meibum secretions onto the lid margin and then into the inferior tear meniscus. If the lipid secretions are balanced an adequate lipid layer is maintained at the air interface to minimize evaporation and prevent dry eye states. If the lipid secretions are inadequate the lipid layer is not adequate to minimize evaporation with resulting rapid evaporation leading to dry eye states. Blockade of meibum secretions results in accelerated evaporation of the aqueous layer which, in turn, causes symptoms such as dryness, scratching, irritation, burning, tearing, redness, and itchiness. These symptoms are typical of the pathological condition known as dry eye. Dry eye causes may include aging, medication side effects, diseases, and eye structure problems.

Treatment of dry eye typically includes eye drops, punctal occlusions, medications, and/or surgery. Most commonly, a lubricating eye drop is used for dry eye treatment. Several prescription medications are also available for increasing tear production. More recently, occlusions of the meibomian gland are treated using heat and possibly gentle agitation to remove one or more occlusions of the meibomian gland and restore normal tear production. While these treatments are somewhat effective at removing occlusions, none address underlying etiology of dry eye—suboptimal transfer of meibum from the meibomian glands to the eye surface.

Thus, there is a need for new methods for treatment or prevention of dry eye syndrome.

BRIEF SUMMARY OF THE INVENTION

The following summary is presented to highlight particular aspects of the invention, and is not a limitation of the devices or processes of the invention.

The processes and apparatuses of the invention have utility as a treatment or prophylaxis for dry eye syndrome and improving secretion of meibum from one or more meibomian glands. Occlusions of the meibomian gland are treated applying light to the outer part of the eyelid at selected locations. As humans age, the areas of the skin tend to lose elasticity, suppleness and softness. Much of these effects can be attributed to a loss in skin collagens or a reduction in fibroblast activity. Occlusions of the meibomian gland are treated applying light to outer part of the eyelid and periorbital region of the eye. The light is applied to the lower eyelid area. Optionally, light is also applied to the periorbital region. In some embodiments the upper eyelid may also be treated by exposure to light. In all cases, the light applied has a predetermined set of photomodulating parameters. The inventors experimentally demonstrate that applying light having a predetermined set of photomodulating parameters to the outer part of the eyelid regenerates collagen and improves eyelid elasticity.

Light is administered to an outer surface of one or more eyelids wherein the light has a predetermined set of photomodulating parameters. The light is not applied to a meibomian gland via the inner eyelid or the region of the inner eyelid proximal to a meibomian gland. Optionally, light is not applied to areas adjacent to an eyelid.

Administration of light to an outer surface of one or more eyelids stimulated activity of the tear (lacrimal) glands situated in the upper and lower outer portions of each orbit/eyelid, stimulating secretion of the aqueous layer of the tear film. The lacriminal gland produces tears, which can wet the surface of the eye reducing the dry eye.

Application of light is optionally, but not necessarily, accompanied by application of eye gentle vibrations to the eyelids and optionally the periorbital region. Optionally, vibrations are excluded from application to one or more eyelids and optionally to a periorbital region. The vibrations are optionally provided by a vibration source that could be associated with the light source. The source of vibrations could be implemented as a segment of perimeter or of the entire perimeter of the light source, optionally in the same instrument. Activation of the source of vibrations, when it is in contact with the eyelid(s) area and periorbital region of the eye, could apply to the eyelid(s) area and optionally the periorbital region of the eye vibrations. Application of such vibrations to the eyelid(s) area and optionally periorbital region of the eye promotes removal of any minor or major blockade of meibomian duct improving secretion of meibum and tears and lubrication of the eye.

An apparatus is provided that is specifically tailored to delivery light of a predetermined photomodulation to one or more eyelids, optionally to the lower eyelid, optionally to both the lower and upper eyelid. The light source operates in a photomodulation mode to emit light of a predetermined photomodulation to activate fibroblasts to create collagen and elastin. The additional collagen and elastin functions to thicken and strengthen the eyelid region, improving tone, and stimulating movement of meibum onto the eye. An apparatus optionally includes one or more light sources, optionally light emitting diodes (LEDs) that emit light with wavelengths being one of a group of wavelengths consisting of 605+/−10 nm, 630+/−10 nm, 660+/−10 nm, and a combination thereof. Light emission is optionally in a pulse mode or a continuous mode for a treatment time. In embodiments where the light is emitted in a pulse mode, the pulses are optionally of 5 milliseconds to 200 milliseconds, or 0.5 milliseconds to 0.100 milliseconds. In embodiments where the light is emitted in a continuous mode, the continuous operation is optionally for a treatment time of 2 minutes to 10 minutes. Optionally, the light source emits light in an alternating, regularly or randomly, in both a pulse mode and a continuous mode. The light emitted by an apparatus optionally has a fluence of between 0.1 J/cm$^2$ to 50 J/cm$^2$. A light source optionally includes a shaping or structure that assists in the placement of the device such that the light source may be held directly on the surface of the skin, or be held a selected distance from the skin. An apparatus optionally includes a vibration source configured to apply vibrations to at least the lower eyelid area of the eye. A vibration source is optionally integrated in the apparatus, or is affixed thereto. When emitting vibrations, an apparatus optionally emits the vibrations having a frequency of 1 Hz to 100 Hz. The vibrations optionally having an amplitude of 0.1 mm to 0.4 mm.

The processes provided may be achieved using an apparatus as provided by the invention.

DETAILED DESCRIPTION OF EMBODIMENTS OF THE INVENTION

Figure 1A:
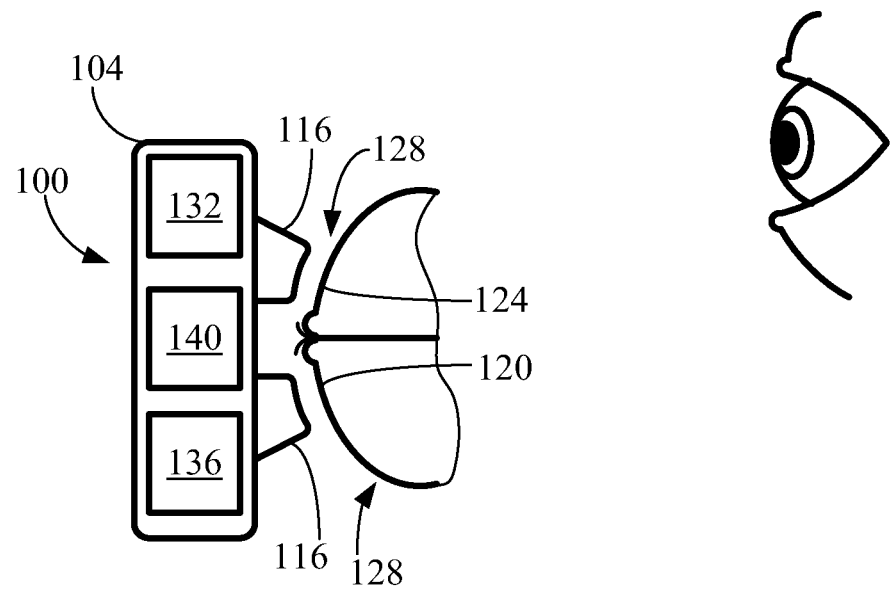
FIG. 1 is a simplified illustration of a dry eye treatment apparatus according to an example illustrating positioning a distance from the surface of the skin (FIG. 1A) or directly contacting the skin (FIG. 1B)

The following description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the processes and devices are described as an order of individual steps or using specific arrangements of elements, it is appreciated that described steps or elements may be interchangeable such that the description of the invention includes multiple parts or steps arranged in many ways as is readily appreciated by one of skill in the art.

The inventions have utility as a treatment or prophylaxis for dry eye syndrome. Processes and apparatuses are provided for improving secretion of meibum from one or more meibomian glands. A process includes administering light to an outer surface of one or more eyelids wherein the light has a predetermined set of photomodulating parameters. The light is not applied to a meibomian gland via the inner eyelid or the region of the inner eyelid proximal to a meibomian gland.

The inventor discovered that dry eye or other conditions caused by suboptimal transfer of meibum from a meibomian gland to the eye can be dramatically improved by modulating the reaction in an eyelid during a blink reflex. As humans age, the areas of the skin tend to lose elasticity, suppleness and softness. Much of these effects can be attributed to a loss in skin collagens or a reduction in fibroblast activity. By improving the condition of the skin of the eyelid, positive effects are transmitted to the underlying meibomian glands leading to improved meibum secretions and a reduction in symptoms of dry eye syndrome.

Skin and other body tissues have the ability to absorb light and use it as a source of energy to stimulate cellular activity. By carefully selecting the wavelength, fluence, irradiance, duration, and continuity of light applied to the outer surface of an eyelid, fibroblast activities can be significantly increased leading to greater production of collagen and elastin. This improves the structure of the eyelid increasing meibum transfer through the meibomian duct and reducing the likelihood of blockage. Without being limited to one particular theory, it is believed that light of a particular wavelength, in the absence or presence of heat, will stimulate mitochondrial ATP production in fibroblasts in the skin. This in turn fuels increased collagen and elastin production regenerating skin elasticity. With increased collagen and elastin levels in the eyelid and optionally areas surrounding the eyelid, proper shaping of the skin is achieved during the blink reflex to promote normal meibum passage through the duct. Processes provided are optionally performed on subjects that do not have a current blockage of the meibomian gland duct and serve to prevent such blockage.

In a process of preventing or treating dry eye syndrome in a subject, light is applied to the skin of the eyelid, and optionally surrounding area, where the light is of a preselected wavelength. Illustrative wavelengths include those operable for increasing fibroblast activity. Such wavelengths are discussed by Webb, et al., *Lasers Surg Med,* 1998; 22(5):294-301 and Lubart, et al., *Laser Therapy,* 1993, 5:55-57. Illustrative wavelengths include 605 nm, 630 nm, 660 nm, or in some embodiments 850-855 nm. In some embodiments, the eyelid is not heated. In these embodiments, light wavelengths and intensities that increase the temperature of the skin are optionally avoided by refraining from use of light in the infrared wavelengths or above, or other application of heat. Optionally, light has a wavelength that is not in excess of 750 nm, optionally, not in excess of 700 nm, optionally not in excess of 690 nm. In some embodiments, light has a wavelength of between 600 to 700 nm. In particularly preferred embodiments, light has a wavelength of 660 nm+/−10 nm. Optionally, light has a wavelength that is 660 nm.

The light optionally has a fluence of between 0.1 to 25 J/cm$^2$. Optionally, a fluence is of 0.1 to 5 J/cm$^2$. Optionally, the fluence is 22-25 J/cm$^2$.

Light is optionally delivered in a pulsed or continuous emission format. In embodiments that employ a pulsed light source, the light optionally has a pulsing pattern with a pulse width of approximately 0.0005 seconds and a pulse interval of approximately 0.00015 seconds. The predetermined pulsing pattern optionally includes pulse trains of between approximately 3 and 5 pulses with pulse train intervals of approximately 0.00155 seconds. It should be understood that other pulsing patterns could be used without departing from the scope of the present invention. Illustrative pulsing mechanisms can be found in U.S. Patent Application Publication No. 2008/0108982.

In some embodiments, light is used with a target irradiance of approximately 0.05 W/cm$^2$ and a target fluence of approximately 4.5 J/cm$^2$. Other irradiance parameters can be found in U.S. Patent Application Publication No. 2008/0108982.

A light source may be held or positioned directly on the surface of the skin or may be held a selected distance from the skin. Optionally, distance from the light source (or light output location) is approximately 0 mm to 3 mm from the skin surface, preferably directly in contact with the skin.

A light source is optionally one or more light emitting diodes capable of emitting light of the desired predetermined set of photomodulating parameters optionally including fluence, wavelength, etc. Optionally a plurality of light sources is used in close proximity to one another. An apparatus operable for achieving prevention or treatment by the processes of the invention and optionally delivering light optionally of any one or all of the parameters herein is described below.

Light is optionally applied to an eyelid or an area proximal to an eyelid. Optionally, light is applied to a lower eyelid below the lash line without light being applied to an upper eyelid. The region proximal to an eyelid includes the orbital region of the face, optionally extending to the zygomatic region. In some embodiments, light is applied to the area of the lower eyelid below the lash line and excludes light application to the upper lid or areas proximal to the lower eyelid. Light is optionally not applied to or is optionally prevented from application to the inner canthus, outer canthus, or both.

In some embodiments, light is applied such that the temperature of the skin does not significantly increase. Optionally, skin temperature is maintained during an application time within +/−2 degrees C.

An application time is optionally between 1 minute and 15 minutes. Optionally, an application time is from 1 to 5 minutes, 2-4 minutes, optionally 3 minutes. It has been found that an application time of three minutes at least twice a week produces excellent results in improving meibum secretion and treating dry eye syndrome.

Light is optionally applied to the eyelid for a treatment time. A treatment time is optionally from one application time to a series of application times that are used daily, weekly, monthly, or as long as desired. Results are achieved after a single application time. Improved results are achieved by daily or weekly use for one or more application times. Daily or weekly light application, optionally twice weekly, will achieve excellent results in 2-12 weeks. As such, therapeutic treatment of dry eye syndrome is achieved after a single or multiple applications of light as described.

In some embodiments, low level heat is simultaneously applied with the light. Optionally, pressure vibration is applied simultaneously with the light. Without being limited to one particular theory, the application of vibration and heat are believe to promote removal of any minor or major blockade of the meibomian duct further improving secretion of meibum and lubrication of the eye. Heating and vibration, if used in addition to the application of light, are optionally as applied as described in U.S. Patent Application Publication No. 2012/0016275.

In some embodiments blockage of the meibomian duct is prevented. Processes of preventing meibomian gland duct blockage include applying light to an outer surface of one or more eyelids or proximal thereto, said light having a predetermined set of photomodulating parameters, said light not directly applied to a meibomian gland or the inner surface of an eyelid, and improving meibomian gland function by the applying. Photomodulating parameters are as described herein for optimizing or increasing fibroblast activity. With improved secretion of meibum, dry eye syndrome is prevented as well as preventing blockade of the meibomian gland duct.

The processes of treating or preventing symptoms or causes of dry eye syndrome are appreciated not to apply light directly to the region of a meibomian gland such as the inner eyelid region. It was surprisingly discovered that light application as described herein could improve secretion of meibum without the need for direct stimulation of the gland itself as is typically done by massage, heat, or direct application of light (for heating purposes). The invention represents a much simpler process for treating or preventing dry eye syndrome or preventing meibomian gland blockage than was appreciated or envisioned in the art. As such, many embodiments of the invention exclude one or more of physical pulsation, application of heat, massage, sonic pulsation, or other prior methods of treating meibomian gland blockage or treatment of dry eye.

Figure 2:
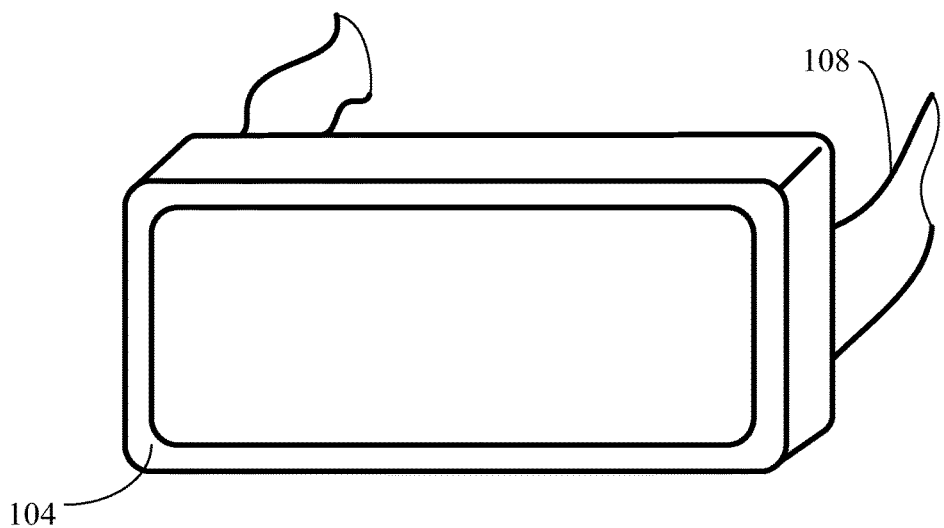
FIG. 2 is a simplified illustration of a dry eye treatment apparatus according to an example.
Figure 3:
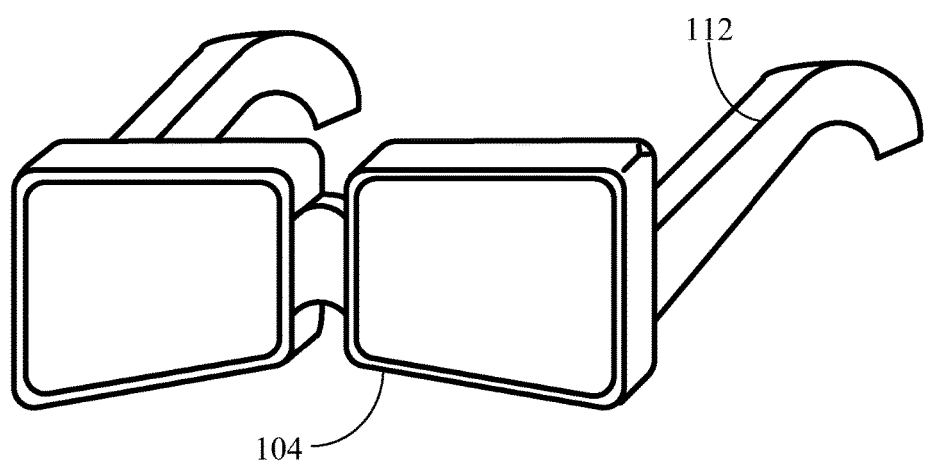
FIG. 3 is a simplified illustration of a dry eye treatment apparatus according to an example.

Also provided are apparatuses for administering light according to a process of increasing secretions from a meibomian gland. In an exemplary embodiment, reference is made to FIG. 1 that illustrates an exemplary dry eye treatment apparatus. Apparatus 100 includes a frame 104 configured to be applied to a facial area of a treatment recipient. In one example, frame 104 could bear swimming goggles or diving mask shape (FIG. 2) and when applied to the facial area of a treatment recipient, the frame could be stabilized in place by flexible straps 208 or temples 308 (FIG. 3). Frame 104 could include one or more light sources 116 configured to apply light to at least one eyelid 120 or 124 area and periorbital region 128 of an eye, a power supply 132 configured to supply power to the at least one of light sources 116 and a controller 136 configured to control power supply 132 and operation of light sources 116. A rechargeable or disposable battery 140 configured to supply power at least to controller 136 and to light sources 116 could also be located in frame 104.

Figure 4:
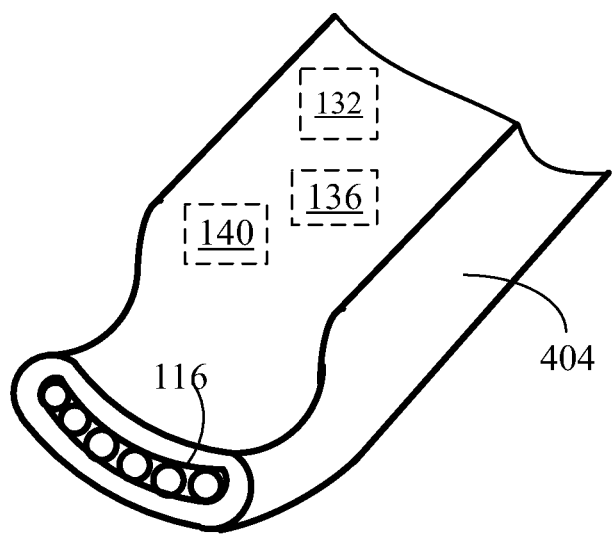
FIG. 4 is a schematic illustration of a light source of a dry eye treatment apparatus according to an example illustrating the light sources in as per the skin facing side of the embodiment of FIG. 2.

In one example, frame 104 configured to be applied to a facial area of a treatment recipient is a wearable frame, worn by the treatment recipient at the time of treatment. In another example, apparatus 100 could be implemented in shape of a handheld body 404 (FIG. 4). Handheld body 404 could have a shape that facilitates the apparatus 100 to the lower or upper eyelid application. Light source 116 could be mounted on one end of the handheld body, typically, the end configured to apply light emitted by light source 116 to at least one eyelid 120 or 124 (FIG. 1) area and periorbital region 128 of an eye. The treatment recipient could locate the handheld body 404 in contact or at a distance from the eyelid at the time of treatment. Similar to frame 104 in addition to light sources 116 handheld body 404 could incorporate a power supply 132 configured to supply power to the at least one of light sources 116 and a controller 136 configured to control power supply 132 and operation of light sources 116. A rechargeable or disposable battery 140 could also be located in handheld body 404.

Figure 5:
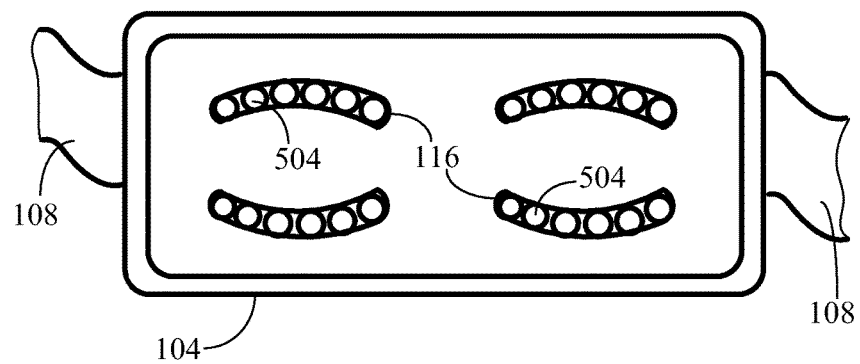
FIG. 5 is a schematic illustration of a light source of a dry eye treatment apparatus according to an example.

In a process of preventing or treating dry eye syndrome in a subject, light is applied to the skin of the eyelid, and optionally surrounding area, where the light is of a preselected wavelength. FIG. 5 is a schematic illustration of light source according to an example. Light source 116 (as viewed from the side of the treatment recipient) could be an assembly of LEDs 504 arranged to match the shape of lower 120 and/or upper 124 eyelids area and periorbital region 128 of the eye. The LEDs could be potted by a transparent or light diffusing epoxy, such that the face of the potting configured to be applied to the eyelids would have a shape matching the shape of the eyelids. In some examples, and in particular when the potting could be a diffusive potting, the outer surface of the potting could exceed the height of the LEDs and illuminate the eyelids with diffused light.

Assembly of LEDs 504 could include different LEDs emitting in a relatively large spectrum from 400 nm to 2200 nm, although in some examples LEDs could be selected to emit light with preselected discrete wavelengths of in some non-limiting examples 605 nm, 630 nm, or 660 nm. Light source 116 could be populated by LEDs emitting a single wavelength, for example 660 nm, 630 nm or 605 nm and a combination of the above wavelengths. The bandwidth of the emitted light could be 20 nm or 40 nm as provided by a particular LED. The preselected wavelengths are far away from the infrared segment of the spectrum and do not cause increase in temperature of the treated skin.

LEDs 504 could emit light in a pulse mode or in a continuous emission mode. When LEDs 504 operate to emit light in the pulse mode, they could emit pulses of 1 millisecond to 200 milliseconds, 5 milliseconds to 100 milliseconds, 0.1 to 20 milliseconds, optionally 0.5 to 10 milliseconds, optionally 0.1 milliseconds to 200 milliseconds or any value or range therebetween. The interval between the pulses could be between 1 millisecond and 100 milliseconds, optionally 0.1 milliseconds to 10 milliseconds. The pulses could be emitted in a predetermined pulse emitting pattern. Optionally, the pulse emitting pattern could include pulse trains of between approximately 3 and 5 pulses. The interval between the pulse trains could vary and be between 5 milliseconds and 50 milliseconds. It should be understood that other pulsing patterns could be used without departing from the scope of the present method.

When LEDs 504 operate to emit light in the continuous mode, the LEDs operate for 1 second to 200 second or operate for 5 second to 600 second. In both pulse and continuous operating mode the light emitted by the LEDs could have a fluence of between 0.1 J/cm$^2$ to 50 J/cm$^2$ and each treatment session could continue for 2 minute to 10 minute.

The inventors experimentally determined that light applied to at least one eyelid area, for example, to lower eyelid area 120 (FIG. 1) and optionally periorbital region (128) of an eye activates fibroblasts to create collagen and elastin thereby thickening and strengthening the periorbital and eyelid area. Optionally, light is applied to a lower eyelid below the lash line without light being applied to an upper eyelid. The region proximal to an eyelid includes the orbital region of the face, optionally extending to the zygomatic region. Optionally, light is not administered or is prevented from contacting the skin in other than that of a lower eyelid. New collagen production, elastin production, and combinations thereof improve eyelid tone (elasticity). The improvement in the eye lid tone (elasticity) facilitates eye blinking process and distribution of meibum and other fluids, such as tears, over the eye surface. Meibum (e.g. containing lipid) secretions form and maintain an adequate lipid layer at the air interface to minimize evaporation of aqueous content of the tears and prevent dry eye states.

The inventors have also noticed that glands evacuate better from the upper eyelids following exposure of the upper eyelid skin to light. Without being bound to one particular theory, it is believed that this is related to gravity that assists evacuation of the tears and removed particles blocking the meibomian duct. Accordingly, in some embodiments of the invention, an apparatus administers light to the upper eyelid that is optionally 20% to 30% less intensive then the treatment applied to the lower eyelid, but sufficient to create a better platform for the upper eyelid particles blocking the meibomian duct evacuation during blinking.

Generally, light source 116 could be operated in an operation mode known as photomodulation. Photomodulation is a term that describes the use of low intensity light therapy to alter (enhance or reduce) the activity of living cells. It is a painless, non-invasive treatment that uses light-emitting diodes (LED) to activate new collagen formation and simultaneously inhibit the breakdown of existing collagen, helping to rejuvenate the skin. New collagen formation, elastin production, and combinations thereof improve eyelid tone (elasticity). The improvement in the eyelid tone (elasticity) facilitates eye blinking process and distribution of meibum and other fluids, for example, tears over the eye surface. Meibum (Lipid) secretions form and maintain an adequate lipid layer at the air interface to minimize aqueous tear component evaporation and prevent dry eye states.

Usually, light-based skin therapies, including intense pulsed light and laser treatments, rely on heat and thermal injury to create changes in skin appearance. Photomodulation does not use heat and there is no trauma to the tissues which means there is no downtime.

However, there are specific sequences of light pulses that activate certain subcellular systems better than others. The reaction of the treatment recipients to photomodulation is individual. Controller 136 (FIG. 1) facilitates setting of specific sequences or parameters of light pulses that activate the desired subcellular systems. The photomodulation parameters could include pulse duration, time between the pulses, total light application time, and others.

Figure 1B:
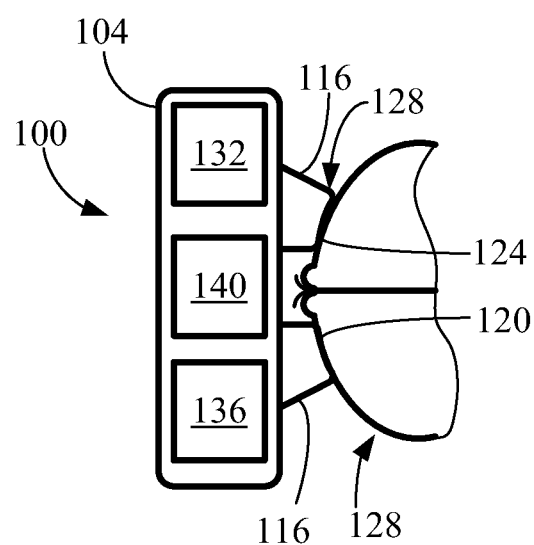

According to one example, light source 116 could be held or located at a selected distance from skin. The distance could be between 1 mm and 5 mm (FIG. 1A). According to another example, light source 116 could be held directly on surface of skin and be in contact with the skin surface (FIG. 1B).

Operation of the light source 116 does not change substantially the temperature of the eyelids. Although when the potting is in contact or applied to the eyelids, the skin temperature could be increased, but as the experiments show it does not increase during the application time of the light on more than 2 degrees C.

According to another example, light source 116 is an incandescent or halogen lamp covered by a filter that transmits a desired or selected wavelength for example, 630 nm or 660 nm and reflects the other wavelengths and in particular wavelength that deliver heat that could increase the temperature of the eyelids. The filter could be a simple colored glass or a transparent glass with a dielectric coating. The filter could be transparent or having one of its sides processed to disperse light.

Figure 6A:
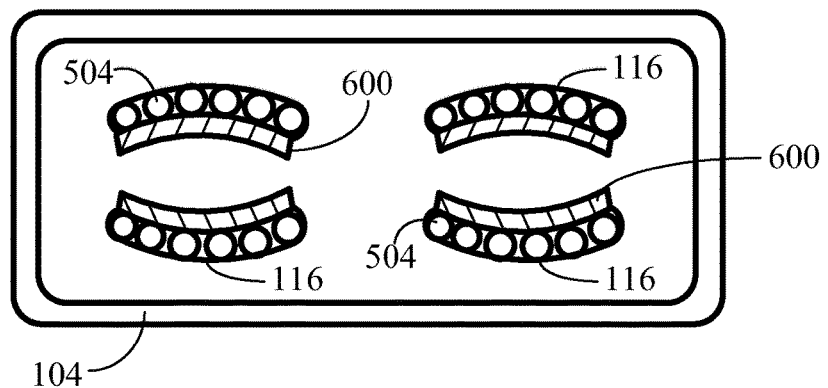
FIG. 6 is a schematic illustration of an optional vibration source of a dry eye treatment apparatus according to an example illustrating vibration sources located outside a plurality of light sources (FIG. 6A), on both sides of a plurality of light sources (FIG. 6B), or on both sides of a set of light sources in an apparatus of a different configuration (FIG. 6C)
Figure 6B:
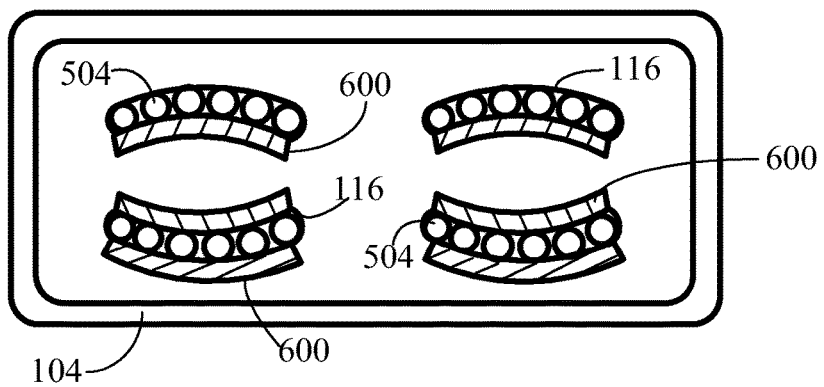
Figure 6C:
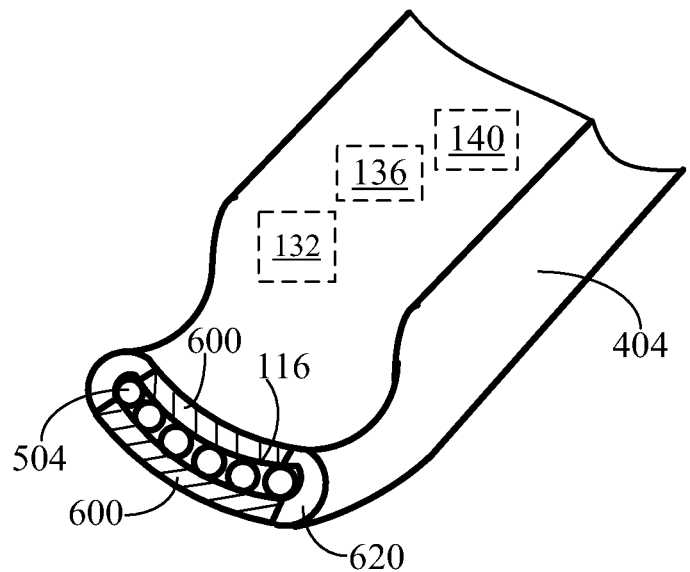

FIG. 6 is a schematic illustration of dry eye treatment apparatus according to an example. Frame 104 of apparatus 100 (FIGS. 6A and 6B) could further include an optional source of vibrations 600 configured to apply gentle vibrations to eyelids 120 and 124 area and periorbital region 128 of the eye. According to one example, the vibration source 600 could be associated with the light source 116. The source of vibrations could be implemented as a frame 608 made of flexible piezoelectric material such as conformable piezoelectric materials commercially available from MIDE, Medford, Mass. 02155, USA or Meggit Sensing Systems A/S, Denmark and deposited about perimeter 412 of light source 116. In another example, frame 408 could be made of conventional piezoelectric material screen printed on a segment of perimeter 612 or almost the entire perimeter of light source 116.

In a similar way, perimeter 620 of apparatus 404 (FIG. 6C) surrounding light source 116 could include a source of vibrations 600 configured to apply gentle vibrations to eyelids 120 and 124 area and periorbital region 128 (FIG. 1) of the eye.

Activation of source of vibration 600 piezoelectric elements 608, when it is in contact with the eyelids 120 and 124 area and periorbital region 128 of the eye, could apply to the eyelids area and periorbital region of the eye vibrations. The amplitude of the vibrations could be 0.005 mm to 0.4 mm, or 0.005 mm to 0.1 mm, and the frequency of the vibrations could be between 1 Hz to 100 Hz. Application of such vibrations to the eyelids area and periorbital region of the eye promotes removal of any minor or major blockage of meibomian duct improving secretion of meibum and lubrication of the eye and more uniform distribution of tears over the eye surface.

Figure 7:
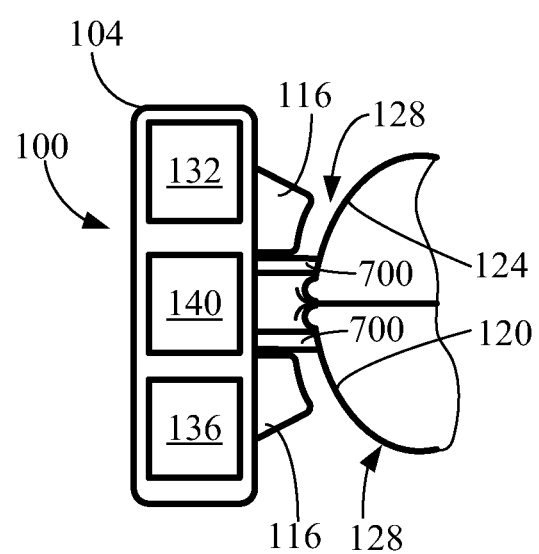
FIG. 7 is a schematic illustration of an optional vibration source of a dry eye treatment apparatus according to an example illustrating variable or fixed supports for adjustments to face shape, or intended distance of the light sources to the skin of a subject.

According to one example, when light source 116 is held or located at a selected distance from skin, source of vibrations 600 could be implemented as an autonomous unit. FIG. 7 is a schematic illustration of dry eye treatment apparatus according to an example. The distance between optional source of vibrations 700 and eyelids 120 and 124 and periorbital area 128 of the eye could be variable to support for adjustments to face shape of the treatment recipient.

In some examples, and particularly when potting is in contact with the eyelid, as noted above a low level heat could be generated by the applied light. Optionally, pressure vibration is applied simultaneously with the light. Without being limited to one particular theory, the application of vibration and gentle heat are believe to promote removal of any minor or major blockage of the meibomian duct further improving secretion of meibum and lubrication of the eye and facilitated more even distribution of tears over the eye surface.

In some examples blockage of the meibomian duct is prevented. The method of preventing meibomian gland duct blockade includes applying light to an outer surface of one or more eyelids or proximal thereto. The light could be applied to the outer surface of one or more eyelids or proximal thereto. The light could have a predetermined set of photomodulating parameters, and the light is not applied directly to a meibomian gland. Photomodulating parameters of the light disclosed herein are generally selected to optimize or increase fibroblast activity. With improved secretion of meibum, dry eye syndrome is prevented as well as prevented is the blockade of the meibomian gland duct.

The method of treating or preventing symptoms or causes of dry eye syndrome are appreciated not to apply light directly to the region of a meibomian and tear glands such as the inner eyelid region. It was surprisingly discovered that light application as described herein could improve secretion of meibum and tears without the need for direct stimulation of the glands themselves as is typically done by massage, heat, or direct application of light (for heating purposes). The disclosed method and apparatus represent a much simpler process for treating or preventing dry eye syndrome or preventing meibomian gland blockade and tear secretion than was appreciated or envisioned in the art. As such, many embodiments of the invention exclude one or more of physical pulsation, application of heat, massage, sonic pulsation, or other prior methods of treating meibomian gland blockade or treatment of dry eye.

The processes provide a simple, rapid, and effective means of treating or preventing dry eye syndrome.

Various aspects of the present invention are illustrated by the following non-limiting examples. The examples are for illustrative purposes and are not a limitation on any practice of the present invention. It will be understood that variations and modifications can be made without departing from the spirit and scope of the invention.

EXAMPLES

Example 1

Ten patients presenting with dry eye syndrome presenting with dryness, itching, irritation or redness, are divided into two treatment groups. Group A of 5 subjects is asked to apply light of 660+/−10 nm using an apparatus essentially as shown in FIG. 4 to the lower eyelid only and below the lash line for three minutes twice weekly. The apparatus is held on the skin surface such that the light sources are less than 3 mm away from the skin surface. The apparatus does not administer heat or pressure to the eyelid. Also, the apparatus does not apply light to either of the eye canthes.

Control Group B consisting of 5 subjects is treated with traditional lubricating eye drops containing 0.4% polyethylene glycol 400 and 0.3% propylene glycol sold as SYSTANE Ultra Lubricant Eye Drops from Alcon Inc., Fort Worth, Tex.

Subjects treated with light therapy show relief of one or more symptoms of dry eye syndrome after a single treatment that continues to improve over the next several. At the end of three weeks of twice-weekly treatment, Group A subjects report little to no dry eye syndrome symptoms. Improvement in dry eye syndrome symptoms is equivalent to subjects of Group B administered traditional therapy.

Various modifications of the present invention, in addition to those shown and described herein, will be apparent to those skilled in the art of the above description. Such modifications are also intended to fall within the scope of the appended claims.

REFERENCE LIST

Almeida-Lopes L., Rigau J., Zangaro R. A., Guidugli-Neto J., Jaeger M. M. Comparison of the low level laser therapy effects on cultured human gingival fibroblasts proliferation using different irradiance and same fluence. Lasers Surg Med. 2001; 29(2):179-84.

Anderson R. R., Parrish J. A. The optics of human skin. J Invest Dermatol. 1981 July; 77(1): 13-9.

Barolet, D., et al., Presented at the ASLMS annual meeting, Orlando, USA, 2005.

Bjerring P., Clement M., Heickendorff L., Lybecker H., Kiernan M. Dermal collagen production following irradiation by dye laser and broadband light source. J Cosmet Laser Ther. 2002 June; 4(2):39-43.

Heickendorff L., Zachariae H., Bjerring P., Halkier-Sorensen L., Sondergaard K. The use of serologic markers for collagen synthesis and degradation in systemic sclerosis. J Am Acad Dermatol. 1995 April; 32(4):584-8.

Karu, T. Molecular mechanism of the therapeutic effect of low-intensity laser irradiation. Lasers in Life Science 1988; 2, 53-74.

Karu T. Primary and secondary mechanisms of action of visible to near-IR radiation on cells. J Photochem Photobiol B. 1999 March; 49(1):1-17. Review.

Kiistala U. Suction blisters device for separation of viable epidermis from dermis. J Invest Dermatol 1968: 50: 129-137.

Saperia, D., Glassberg, E., Lyons, R. F., Abergel, R. P., Baneux, P., Castel, J. C., Dwyer, R. M., and Uitto, J. (1986). Demonstration of elevated Type I and Type II procollagen mRNA levels in cutaneous wounds treated with heliumneon laser. Proposed mechanism for enhanced wound healing. Biochemical and Biophysical Research Communications 138, 1123-1128.

Skinner S. M., Gage J. P., Wilce P. A., Shaw R. M. A preliminary study of the effects of laser radiation on collagen metabolism in cell culture. Aust Dent J. 1996 June; 41(3):188-92.

Smith K. C. Photobiology and photomedicine: the future is bright. J Invest Dermatol. 1981 July; 77(1):2-7.

Sommer A. P., Pinheiro A. L., Mester A. R., Franke R. P., Whelan H. T. Biostimulatory windows in low-intensity laser activation: lasers, scanners, and NASA's light-emitting diode array system. J Clin Laser Med Surg. 2001, February; 19(1):29-33.

Nussbaum E. L, Biemann I., Mustard B. Comparison of ultrasound/ultraviolet-C and laser for treatment of pressure ulcers in patients with spinal cord injury. Physical Therapy 1994(74):812-23.

Yu W., Naim J. O., Lanzafame R. J. The effect of laser irradiation on the release of bFGF from 3T3 fibroblasts. Photochem Photobiol. 1994 February; 59(2):167-70.

Webb C., Dyson M., Lewis W. H. Stimulatory effect of 660 nm low level laser energy on hypertrophic scar-derived fibroblasts: possible mechanisms for increase in cell counts. Lasers Surg Med 1998; 22(5):294-301.

Wheeland R. G. Lasers for the stimulation or inhibition of wound healing. Journal of Dermatologic Surgery & Oncology 1993 (19): 747-52.

Whelan H. T., Smits R. L. Jr, Buchman E. V., Whelan N. T., Turner S. G., Margolis D. A., Cevenini V., Stinson H., Ignatius R., Martin T., Cwiklinski J., Philippi A. F., Graf W. R., Hodgson B., Gould L., Kane M., Chen G., Caviness J., Effect of NASA light-emitting diode irradiation on wound healing., J Clin Laser Med Surg. 2001 December; 19(6):305-14. Review.

Zhang Y., Song S., Fong C. C., Tsang C. H., Yang Z., Yang M. cDNA microarray analysis of gene expression profiles in human fibroblast cells irradiated with red light. J Invest Dermatol. 2003 May; 120(5):849-57.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof.

The invention claimed is:

1. A process for improving meibomian gland function in a subject in need thereof comprising:
applying light emitted from a treatment apparatus to an outer surface of one or more eyelids of said subject, said light having a predetermined set of photomodulating parameters comprising emitting light, said light consisting of one or more wavelengths from 605 nm+/−10 nm to 700 nm+/−10 nm, and
increasing secretion of meibum transfer through a meibomian duct;
wherein the one or more eyelids of said subject are not heated above 2 degrees Celsius from physiological temperature.

2. The process of claim 1 where said light consists of a wavelength of 660 nm+/−10 nm.

3. The process of claim 1 wherein said applying is 1 to 5 minutes per treatment.

4. The process of claim 1 where said step of administering light increases secretion of meibum through a meibomian duct relative to the secretion level in the absence of a blockade prior to said step of applying.

5. The process of claim 1 further comprising applying said light to the surface of skin in the region of the zygomatic process.

6. The process of claim 1 wherein said light consists of the wavelengths of 605 nm+/−10 nm, 630+/−10 nm, 660+/−10 nm, or combinations thereof.

7. The process of claim 1 where said light does not have a wavelength in excess of 690 nm.

8. The process of claim 1, said light further comprising a fluence of between 0.1 to 25 J/cm$^2$.

9. The process of claim 1 where said light has a target irradiance of 0.05+/−0.02 W/cm$^2$.

10. The process of claim 1 where said light is pulsed.

11. The process of claim 10 where said light has a pulsing pattern with a pulse width of 0.0005 seconds and a pulse interval of 0.00015 seconds.

12. The process of claim 10 where said light includes pulse trains of between 3 and 5 pulses.

13. The process of claim 1 further comprising applying vibrations to at least a lower eyelid area and periorbital region of an eye.

14. The process of claim 13 where the amplitude of said vibrations is from 0.1 mm to 0.4 mm.

15. An apparatus for thickening and strengthening the skin of the eyelid, said apparatus comprising:
at least one light source configured to apply light to at least a lower eyelid area of an eye, said light source operating in a photomodulation mode that activates fibroblasts to create collagen and elastin thereby thickening and strengthening said eyelid area, said photomodulation mode comprising emitting light consisting of one or more wavelengths from 605 nm+/−10 nm to 700 nm+/−10 nm.

16. The apparatus of claim 15, wherein the light source is an assembly of LEDs emitting light with wavelengths being one of a group of wavelengths consisting of 605+/−10 nm, 630+/−10 nm, 660+/−10 nm, and a combination thereof.

17. The apparatus of claim 15, where when the light source operates ii the pulse mode and the light source emits pulses of 5 milliseconds to 200 milliseconds, or 0.5 milliseconds to 0.100 milliseconds.

18. The apparatus of claim 15, where said light has a fluence of between 0.1 J/cm$^2$ to 50 J/cm$^2$.

19. The apparatus of claim 15 further comprising a source of vibrations configured to apply vibrations to at least the lower eyelid area of the eye.

20. The apparatus of claim 19, said vibrations having an amplitude of 0.1 mm to 0.4 mm.

* * * * *

UNITED STATES PATENT AND TRADEMARK OFFICE
CERTIFICATE OF CORRECTION

PATENT NO. : 10,272,256 B2
APPLICATION NO. : 14/411631
DATED : April 30, 2019
INVENTOR(S) : Rolando Toyos Page 1 of 1

It is certified that error appears in the above-identified patent and that said Letters Patent is hereby corrected as shown below:

In the Claims

Column 12, Claim 17, Line 63, after "operates", delete "ii" and insert --in--, therefor.

Signed and Sealed this
Twenty-fifth Day of June, 2019

Andrei Iancu
*Director of the United States Patent and Trademark Office*